(12) United States Patent
Berger et al.

(10) Patent No.: US 12,344,421 B2
(45) Date of Patent: Jul. 1, 2025

(54) CLOSING APPARATUS FOR CLOSING PHARMACEUTICAL CONTAINERS

(71) Applicant: Syntegon Technology GmbH, Waiblingen (DE)

(72) Inventors: Tobias Berger, Crailsheim (DE); Ulrich Krauss, Ilshofen (DE); Markus Ilgenfritz, Feuchtwangen (DE)

(73) Assignee: Syntegon Technology GmbH, Waiblingen (DE)

( * ) Notice: Subject to any disclaimer, the term of this patent is extended or adjusted under 35 U.S.C. 154(b) by 182 days.

(21) Appl. No.: 18/251,297

(22) PCT Filed: Aug. 5, 2021

(86) PCT No.: PCT/EP2021/071895
§ 371 (c)(1),
(2) Date: May 1, 2023

(87) PCT Pub. No.: WO2022/096169
PCT Pub. Date: May 12, 2022

(65) Prior Publication Data
US 2023/0406561 A1    Dec. 21, 2023

(30) Foreign Application Priority Data

Nov. 5, 2020    (DE) .................... 10 2020 129 169.8

(51) Int. Cl.
*B65B 55/19*    (2006.01)
*B65B 3/00*    (2006.01)
*B65B 7/28*    (2006.01)

(52) U.S. Cl.
CPC .............. *B65B 55/19* (2013.01); *B65B 3/006* (2013.01); *B65B 7/2821* (2013.01)

(58) Field of Classification Search
CPC . B65B 7/28–2857; B65B 55/19; B65B 3/006; A61L 2202/18; A61L 2202/21; A61L 2/022
See application file for complete search history.

(56) References Cited

U.S. PATENT DOCUMENTS 3,191,354 A * 6/1965 McElroy .................. B67B 3/24
53/331.5
3,220,153 A * 11/1965 Cormack, Jr. ............ B67B 3/24
53/474

(Continued)

FOREIGN PATENT DOCUMENTS

CN    107670081 A    2/2018

OTHER PUBLICATIONS

German Patent Office Action for Related Application 102020129169.8 dated May 28, 2021 (6 pages, including an English statement of relevance).

(Continued)

*Primary Examiner* — Anna K Kinsaul
*Assistant Examiner* — Himchan Song
(74) *Attorney, Agent, or Firm* — Michael Best & Friedrich LLP (57) ABSTRACT

The invention relates to a closing apparatus for closing pharmaceutical containers, having a closing tool for joining a closure element to a pharmaceutical container (68), having a fluid unit for applying at least one gaseous fluid to the container, the fluid unit having at least one filter (64, 66), wherein the closing apparatus has a tool receptacle (14) and a tool unit (18), wherein the tool unit (18) is designed as a module which is repeatedly detachable from and connectible to the tool receptacle (14) by means of a coupling device (16) and which comprises the closing tool, the fluid unit and the at least one filter (64, 66).

8 Claims, 6 Drawing Sheets

(56) References Cited

U.S. PATENT DOCUMENTS

| | | | | |
|---|---|---|---|---|
| 3,299,607 | A * | 1/1967 | Dopp | B65B 31/046 |
| | | | | 426/404 |
| 3,868,917 | A * | 3/1975 | Arfert | B29C 57/12 |
| | | | | 53/486 |
| 5,335,810 | A * | 8/1994 | Holloway | B65B 7/2807 |
| | | | | 221/10 |
| 5,641,004 | A | 6/1997 | Py | |
| 6,199,350 | B1 * | 3/2001 | Brechel | B65B 7/2821 |
| | | | | 53/308 |
| 7,930,867 | B2 * | 4/2011 | Carvin | B65B 31/00 |
| | | | | 53/76 |
| 10,067,151 | B2 | 9/2018 | Procyshyn et al. | |
| 10,807,744 | B1 * | 10/2020 | Seiver | B67B 3/2013 |
| 2011/0094619 | A1 * | 4/2011 | Steel | B65B 55/02 |
| | | | | 24/457 |
| 2015/0266600 | A1 * | 9/2015 | Haimi | B65B 31/046 |
| | | | | 53/404 |
| 2019/0016484 | A1 * | 1/2019 | Diaz Guerrero | B65B 57/02 |
| 2019/0152631 | A1 * | 5/2019 | Sireix | B65B 7/2878 |
| 2019/0177017 | A1 * | 6/2019 | Scott | B65B 31/041 |
| 2019/0233182 | A1 * | 8/2019 | Sibley | A61J 1/03 |
| 2019/0330038 | A1 * | 10/2019 | Melrose | B65B 7/2835 |
| 2020/0338765 | A1 | 10/2020 | Gohier | |
| 2023/0406561 | A1 * | 12/2023 | Berger | B65B 55/19 |

OTHER PUBLICATIONS

International Search Report and Written Opinion for Related Application No. PCT/EP2021/071895 dated Nov. 26, 2021 (11 pages, including an English translation of the ISR).

* cited by examiner

CLOSING APPARATUS FOR CLOSING PHARMACEUTICAL CONTAINERS

BACKGROUND

The invention relates to a closing apparatus for closing pharmaceutical containers, having a closing tool for joining a closure element to a pharmaceutical container, and having a fluid unit for applying at least one gaseous fluid to the container, wherein the fluid unit has at least one filter.

Closing apparatuses of the type mentioned above are used in particular for closing syringes, cartridges and vials. If such containers are filled with a highly reactive filling material, there is a risk that this filling material will react with oxygen. To avoid this, a protective gas is applied to partially filled containers with the aim of ensuring that as little oxygen as possible remains in the container (that is to say above the fill level of the filling material) after a closure element has been joined or placed on the container. To prevent foreign bodies from being transported together with the protective gas into the container, the protective gas is passed through an appropriate filter.

It is also known to apply negative pressure to the space in the container above the fill level of the filling material, for example to simplify the introduction of the protective gas. If the filling material is a toxic active substance, it is known to use a filter near the container if a negative-pressure gas or a partial vacuum is used, to prevent toxic gases from escaping from the container into an external area, for example in the area of a negative-pressure supply.

In order to prevent the introduction of germs into the container during the closing process under the above-mentioned conditions, it is necessary to first sterilize fluid lines of the fluid unit and the at least one filter outside a closing station. The sterilized parts are then brought into a clean room area of a closing station, where they are assembled using glove intervention. This process must be repeated each time a change is made to a new filling material, especially if toxic filling material was previously processed.

The removal, sterilization and installation of a large number of parts (fluid lines, filters) via glove intervention is time-consuming and error-prone. The procedure explained above and practiced in the prior art is also not optimal from the point of view of occupational safety.

SUMMARY

On this basis, the present invention addresses the problem of specifying a closing apparatus which allows simplified handling.

In the closing apparatus according to the invention, a tool unit designed as a module is provided. This module allows simultaneous handling of the closing tool, fluid unit and filter. The module, together with the aforementioned components, can be connected to or detached from a tool receptacle, specifically by means of a coupling device. In other words, the assembly and disassembly process are limited to connecting the tool unit to the tool receptacle via the coupling device and disconnecting the tool unit from the tool receptacle, respectively. A tool unit removed from the tool receptacle can be handled, in particular cleaned, outside a closing station, wherein it is possible that individual components are removed from the module, for example the at least one filter, in this state in which the module is removed from the tool receptacle.

The tool receptacle can also be decontaminated, in particular by simply flowing a decontamination agent through it, for example hydrogen peroxide. Further sterilization is not necessary, since the components of the tool unit are sterilized, since the tool unit carries the at least one filter, and since this filter prevents the introduction of germs into an area fluidically downstream of the at least one filter when the tool unit is in the state coupled to the tool receptacle.

In a preferred embodiment, the coupling device has a coupling element and a coupling element receptacle, which interact form-fittingly in a state coupled to one another. One of the components, for example the coupling element, is associated with the tool receptacle, while the other component, for example the coupling element holder, is associated with the tool unit. A reverse arrangement is also possible. The form fit of said components of the coupling device allows a simple and precise connection of the tool unit to the tool receptacle, so that a possibly automated movement of the tool receptacle can be transferred in a simple manner into a corresponding movement of the tool unit.

It is further preferred that the tool receptacle comprises an actuating device for switching the coupling device between a locking state, in which the module is connected to the tool receptacle, and a release state, in which the module is releasable from the tool receptacle. In this way, the actuation of the coupling device can be shifted into the area of the tool receptacle, thus simplifying the construction of the tool unit.

It is further preferred that the module comprises at least one fluid connection, that the tool receptacle comprises at least one fluid supply device, and that the at least one fluid connection and the fluid supply device are fluidically connected to each other in a state in which the module and the tool receptacle are connected to each other. In other words: by coupling the tool unit to the tool receptacle, the fluid unit of the tool unit is simultaneously connected to the fluid supply device without the need for further joining operations.

It is also preferred that the tool receptacle comprises an actuator for actuating the closing tool. This has the advantage that the tool unit does not require its own actuating device for actuating the closing tool; thus, no control or power supply needs to be provided for the tool unit. This leads to a further simplified design of the tool unit and to a further simplified cleanability.

According to the invention, the fluid unit is designed to apply at least two different gaseous fluids to the container. This means that the tool unit has at least two fluid connections which are supplied with at least two different gaseous fluids via the fluid supply device of the tool receptacle.

According to the invention, it is further provided that the module comprises at least two filters, each of which interacts with one of the different gaseous fluids. These at least two filters can also be handled together with the module, that is to say can be removed together from the closing apparatus when the tool unit is disassembled from the tool receptacle and can be sterilized elsewhere, if necessary with disassembly of the filters.

A combination of gaseous fluids in the form of a negative-pressure gas and in the form of a protective gas is preferred. A negative-pressure gas means a vacuum or partial vacuum. The protective gas is an inert gas, for example nitrogen.

It is also preferable if the tool receptacle is held on a robot arm. This allows the handling (in the sense of a positioning) of the tool receptacle and—when the tool unit is coupled to the tool receptacle—also the handling of the tool unit and thus in particular also of the closing tool. It is possible that such a robot arm delimits an interior space in which parts of the fluid supply device, i.e. in particular fluid lines, possibly also valves or further devices, are arranged. Thus, the surfaces of the closing apparatus that are exposed in the area of a closing station adjacent to a pharmaceutical container to be closed can be limited to the outer surface of the robot arm, the tool receptacle and the tool unit. This allows greatly simplified cleaning of a closing station or of the components of the closing apparatus.

Furthermore, it is preferred if the closing apparatus has a handling device for handling the module. This handling device is a device separate from the aforementioned robot arm, which allows the positioning of the tool unit relative to the tool receptacle. This handling device can, for example, be a second robot arm.

BRIEF DESCRIPTION OF THE DRAWINGS

Further features and advantages of the invention are the subject of the following description and the graphic representation of a preferred exemplary embodiment.

In the drawing

DETAILED DESCRIPTION

A closing apparatus for closing pharmaceutical containers is denoted in the drawing as a whole by the reference sign 10. The closing apparatus 10 is arranged in the area of a closing station of a filling facility and, in particular, is arranged in a clean room. The closing apparatus 10 has a robot arm 12, shown schematically in FIG. 1, which holds a tool receptacle 14. The tool receptacle 14 is repeatedly detachable from and connectable to a tool unit 18 via a coupling device 16.

Figure 1:
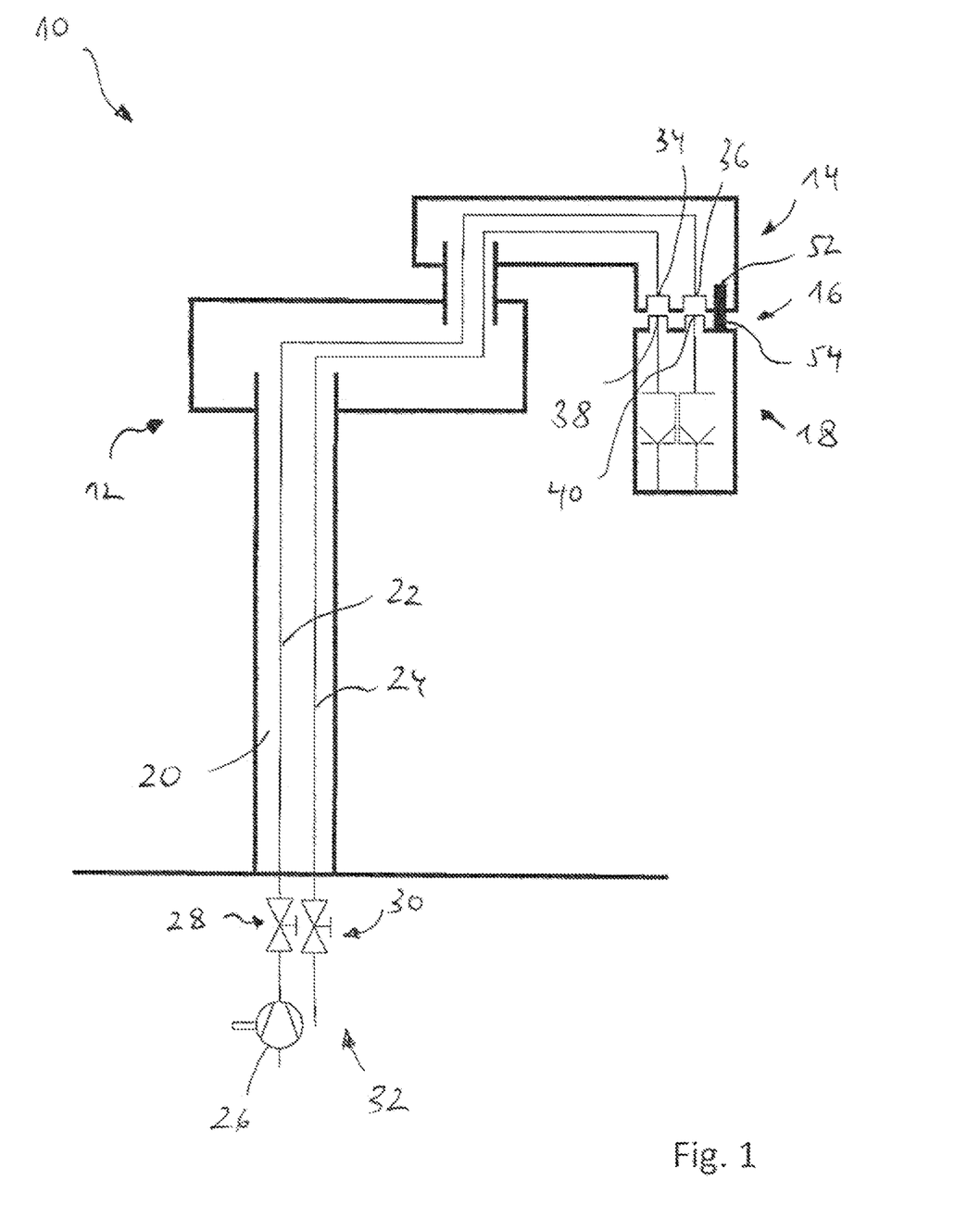
FIG. 1 shows a schematic view of an embodiment of a closing apparatus.

The robot arm 12 has an interior 20, in which fluid lines 22, 24 for different gaseous fluids are arranged. The fluid line 22 serves to conduct a vacuum. For this purpose, the fluid line 22 is connectable to a vacuum pump 26, specifically using a first switching valve 28. A second switching valve 30 serves to introduce a protective gas, in particular nitrogen, into the fluid line 24 or to block such an introduction. The components 20 to 30 together form a fluid supply device 32, which extends into an area of the tool receptacle 14 facing the coupling device 16. There, the tool receptacle 14 has various supply connections 34 and 36 that can be coupled to corresponding fluid connections 38 and 40, respectively, of the tool unit 18.

Figure 2:
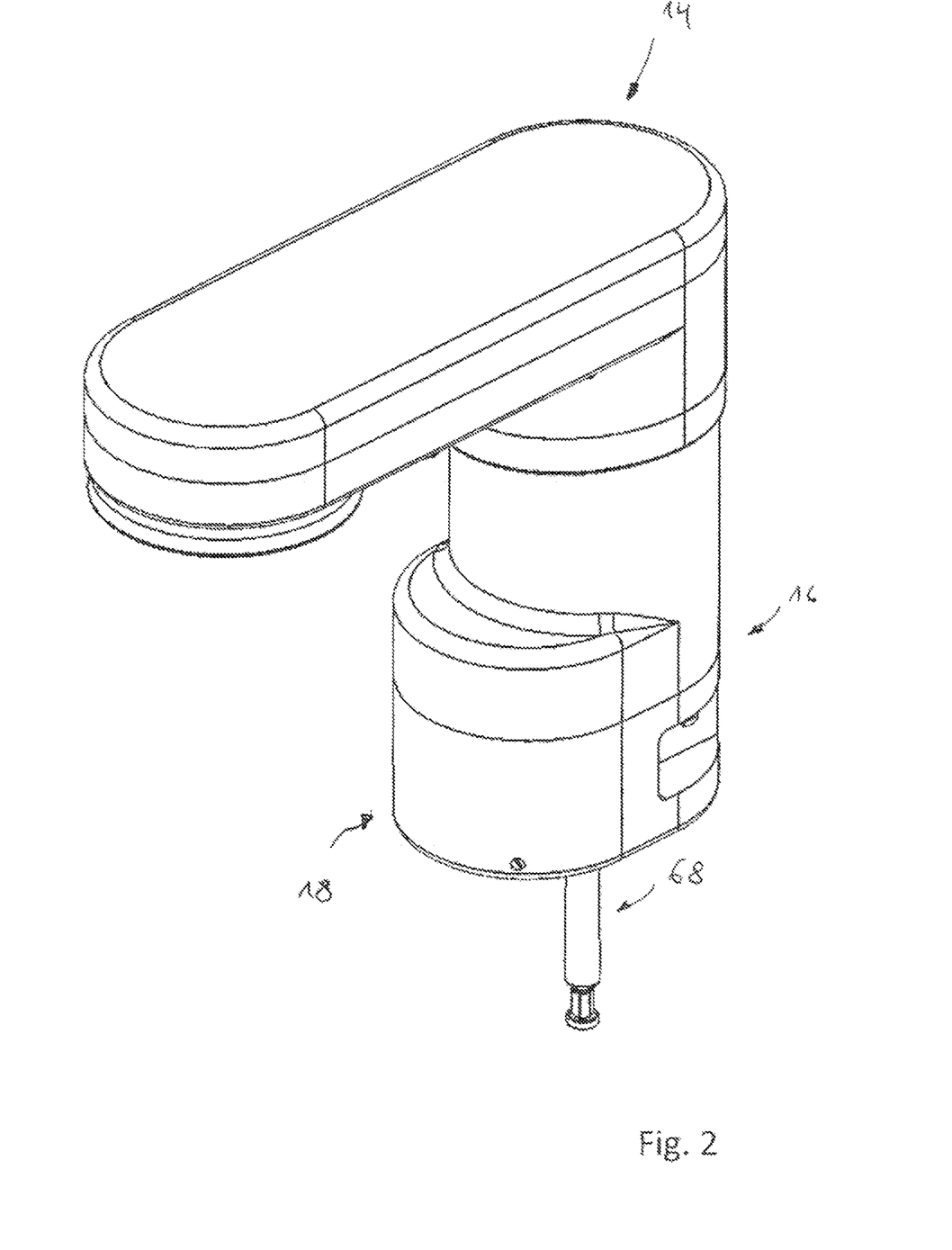
FIG. 2 shows a perspective view of a tool receptacle and of a tool unit of the closing apparatus according to FIG. 1, in a state coupled to one another.

The structure of the tool receptacle 14, the coupling device 16 and the tool unit 18 is explained below with reference to FIGS. 2 to 4. Here, FIG. 2 shows a state in which the tool unit 18 is connected to the tool receptacle 14. The tool unit 18 is used to close a pharmaceutical container 68 shown in FIGS. 2, 3, 5 and 6 by means of a closing tool 42 shown in FIGS. 5 and 6.

Figure 3:
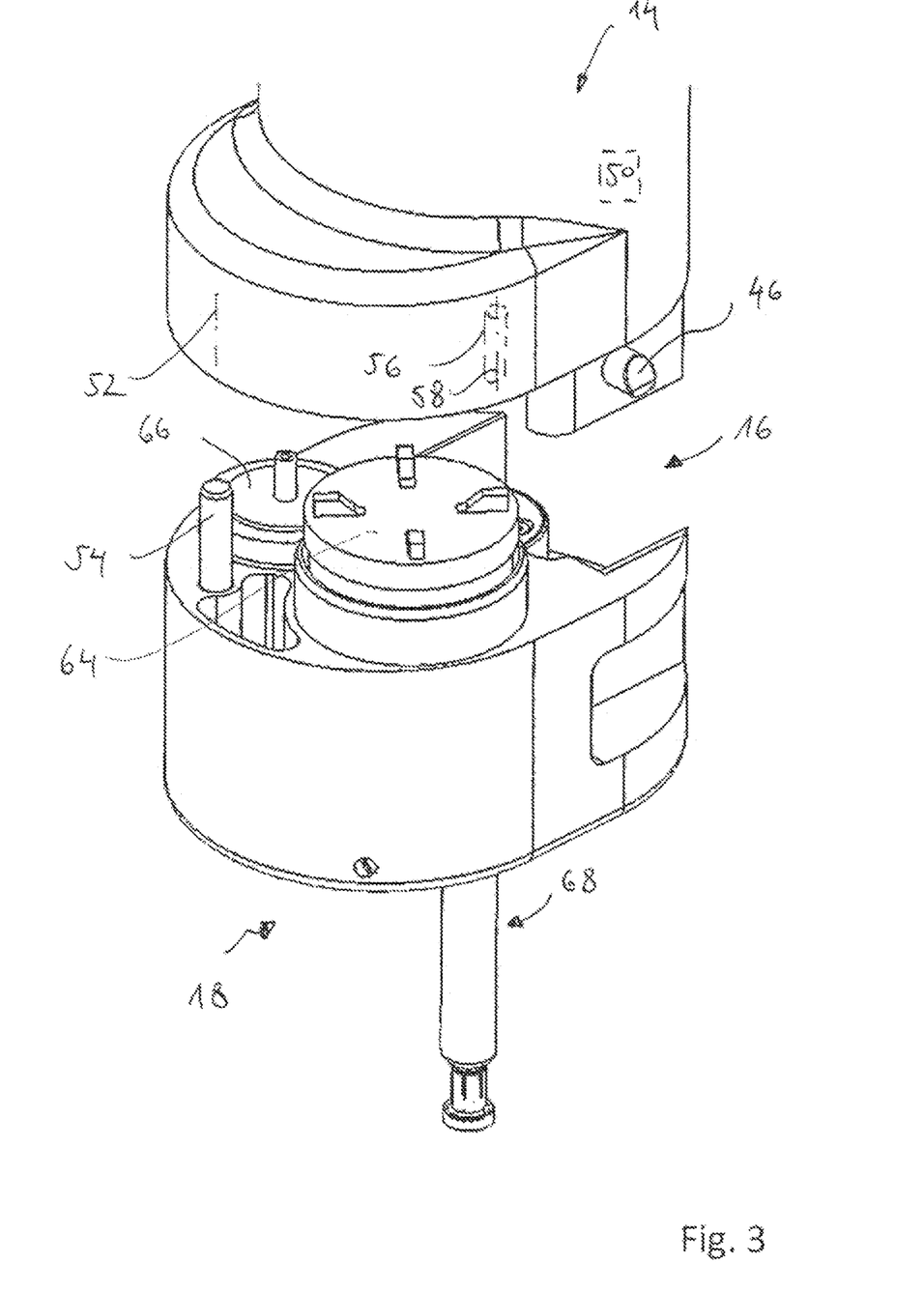
FIG. 3 shows a view corresponding to FIG. 2, in a decoupled state of the tool receptacle and the tool unit.
Figure 4:
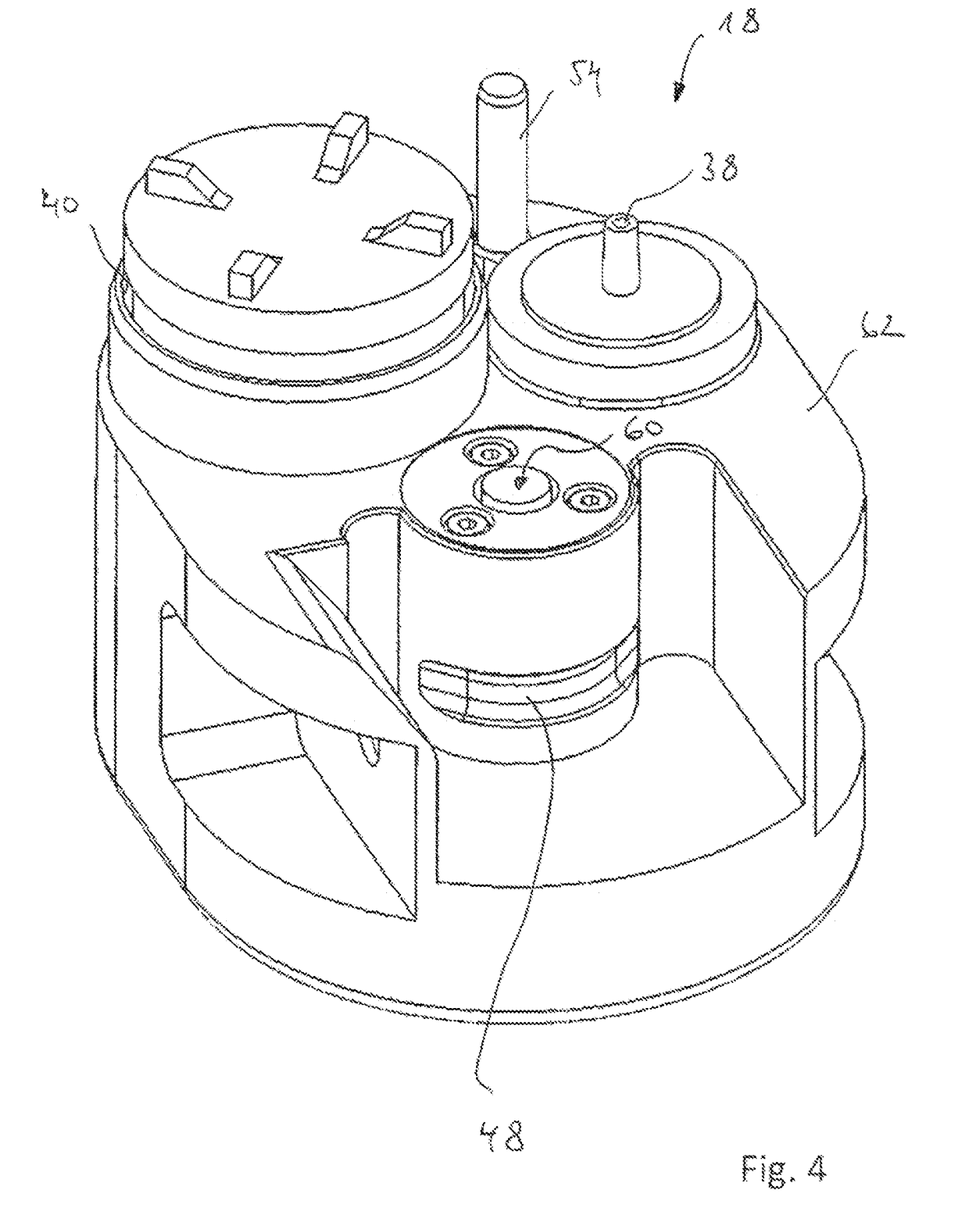
FIG. 4 shows a perspective view of the tool unit.

The coupling device 16 comprises a coupling element 46, compare FIG. 3, which cooperates with a coupling element receptacle 48 of the tool unit 18, compare FIG. 4, in a locking state of the coupling device 16 shown in FIG. 2. The coupling element 46 is formed, for example, as a stud which cooperates with a coupling element receptacle 48 in the form of a groove.

The coupling element 46 is preferably arranged on the tool receptacle 14 and can be actuated by means of an actuating device 50 shown only schematically. When the coupling element 46 is actuated, it is moved relative to the tool receptacle 14 and relative to the coupling element receptacle 48, so that the coupling device assumes a locking state (compare FIG. 2) or a released state, compare FIG. 3.

The tool receptacle 14 further comprises a receptacle bushing 52, indicated by a dot-and-dash line in FIG. 3, which serves to receive a pin 54 of the tool unit 18. The connection between the components 52 and 54 supports the above-explained form-fitting connection of the tool unit 18 and of the tool receptacle 14 by means of the coupling device 16.

Figure 5:
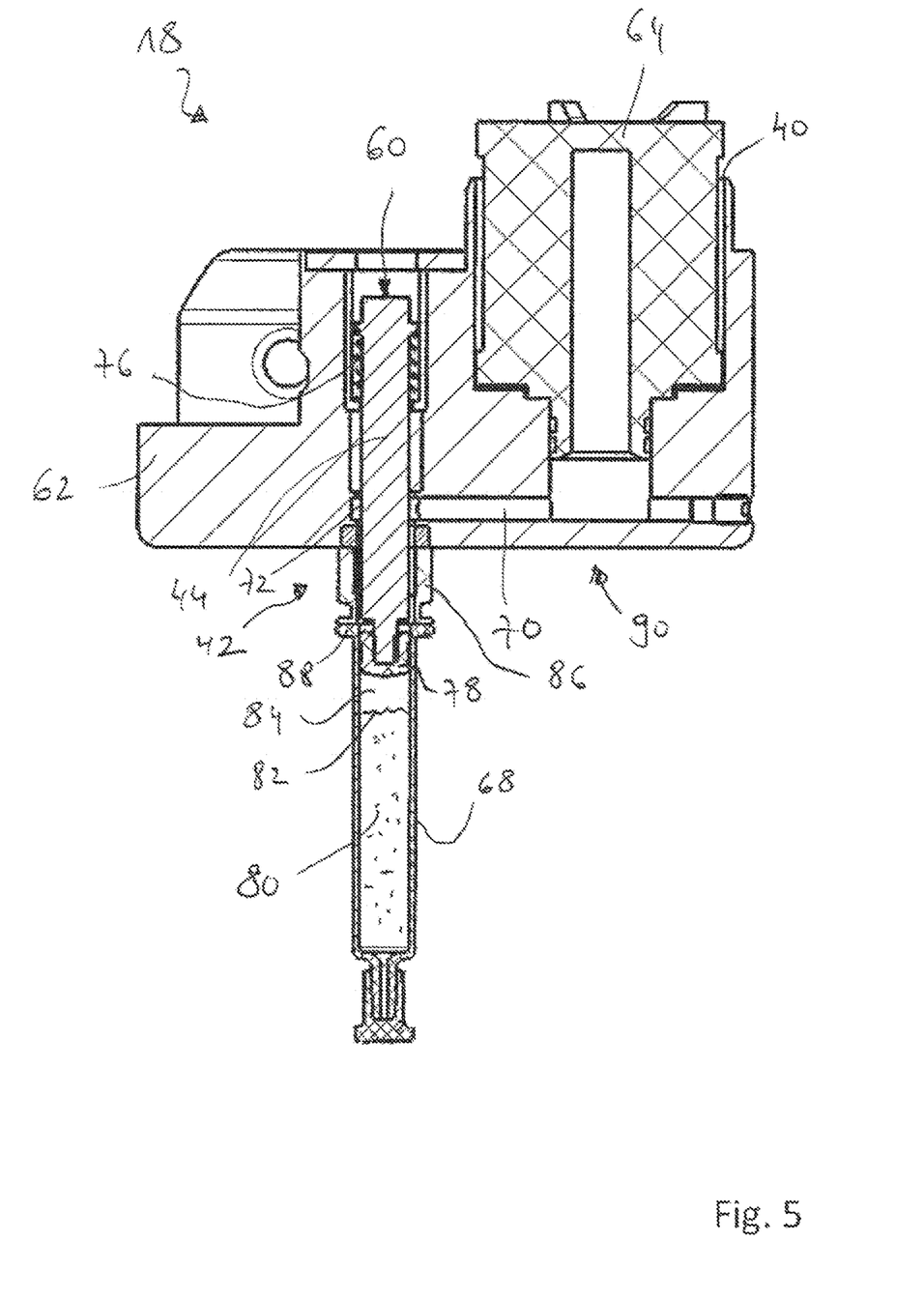
FIG. 5 shows a sectional view of the tool unit along a first sectional plane.
Figure 6:
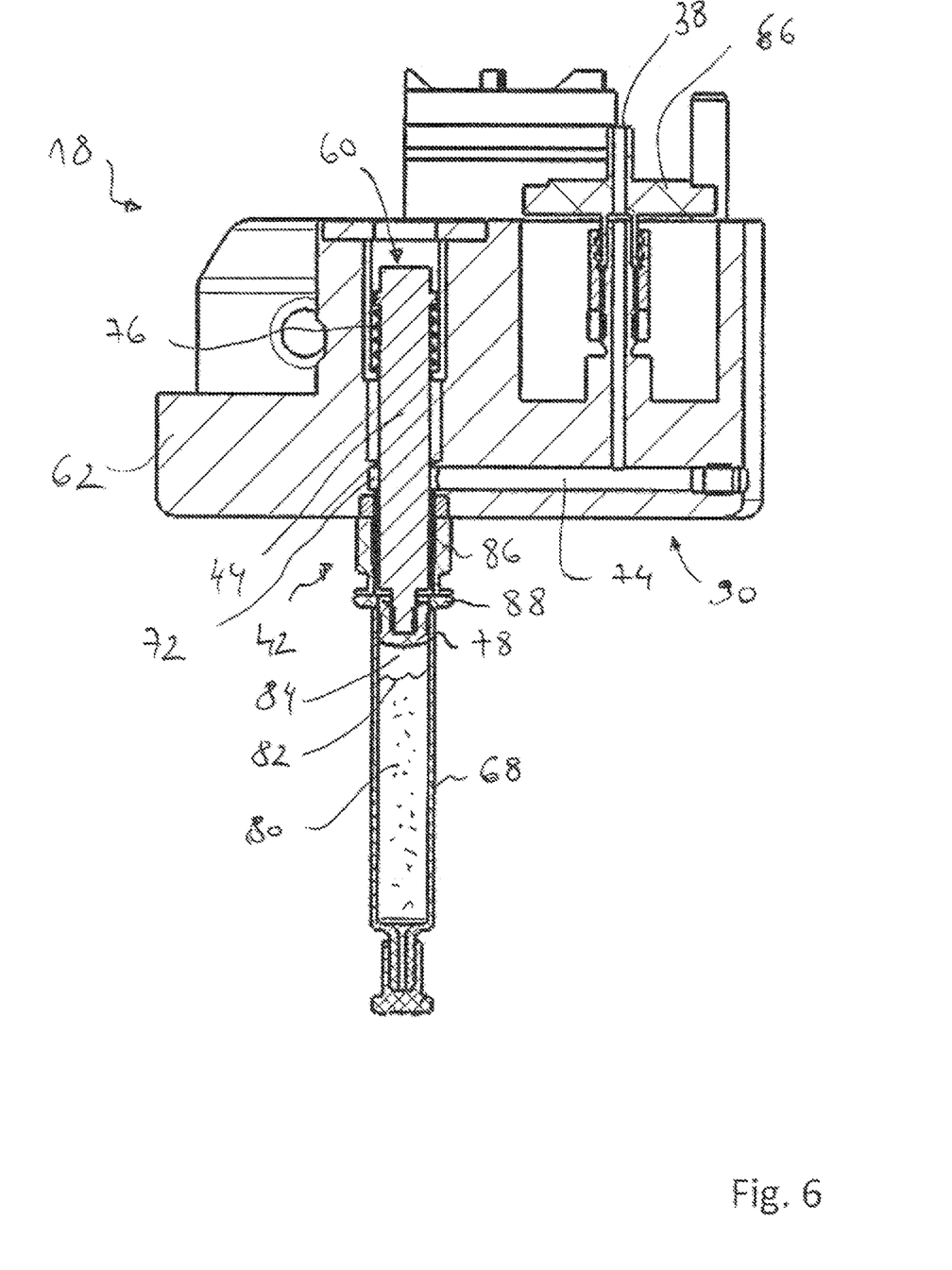
FIG. 6 shows a sectional view of the tool unit along a second sectional plane offset at an angle to the first sectional plane.

The tool receptacle 14 further comprises an actuator 56, indicated by dashed lines in FIG. 3, which is movable along an actuator axis 58 and thus actuates an actuating surface 60 of the closing tool 42, compare FIGS. 4, 5 and 6.

The further construction of the tool unit 18 is described below with reference to FIGS. 4, 5 and 6.

The tool unit 18 is designed as a module which has a housing 62. The housing 62 serves for the arrangement and positioning of components described below. In particular, the housing 62 comprises the fluid connections 38 and 40 already mentioned with reference to FIG. 1, and the closing tool 42. Further, with respect to the fluid supply device 32 downstream of the fluid connections 38 and 40, respective filters 64 (compare FIG. 5) and 66 (compare FIG. 6) are provided.

A first filter 64 is designed as a sterile filter. The filter 64 prevents any toxic gases from entering the area of the fluid supply device 32 or an external area of the closing apparatus 10 from an interior of a pharmaceutical container 68 to be closed. The filter 64 is thus associated with the negative-pressure gas or vacuum or partial vacuum of the fluid supply device 32.

A second filter 66 is associated with the protective gas, for example nitrogen. The filter 66 prevents foreign bodies from being introduced from the fluid supply device 32 into the container 68.

The first filter 64 is assigned to a fluid path which leads via a first branch line 70 to an annular collection chamber 72, compare FIG. 5. A corresponding second branch line 74 is provided for a protective gas fed to the second filter 66 and also opens out at the collection chamber 72, compare FIG. 6.

The collection space 72 extends annularly around a stopper plunger 44 of the closing tool 42. The stopper plunger 44 is force-loaded by means of a compression spring 76, so that the stopper plunger 44 is held in a basic position in the direction of the tool receptacle 14, so that the actuating surface 60—correspondingly to FIG. 4—is arranged further away from the container 68 to be closed than in an actuating state shown in FIGS. 5 and 6. In this actuation state, the actuator 56 presses on the actuation surface 60 so that the actuation plunger 44 presses a closure element 78, for example a stopper, into an open end region of the container 68.

The container 68 is, for example, provided in the form of a syringe, a cartridge or a vial. The container 68 is preferably held on holders (not shown in the drawing) in such a way that an end region of the container 68 which is initially open and is to be closed points upwards in relation to the direction of gravity.

The container 68 serves to receive a pharmaceutical filling material 80 having an upper fill level 82. A space 84 remains between the fill level 82 and an upper, initially open boundary of the container 68. Prior to insertion of the closure element 78 into the initially open end region of the container 68, the closure element 78 is already received on the stopper plunger 44. However, the stopper plunger 44 is initially still in its upper basic position (cf. FIG. 4), in which the actuating surface 60 is arranged further up, so that the closure element 68 is initially still arranged outside the container 68.

The closure element 78 is then initially still arranged at the level of a sealing connection piece 86, which is connected at one end to the tool unit 18 and at the other end rests against an end flange 88 of the container 68. The sealing connection piece 86 is hollow on the inside and is dimensioned such that the closure element 78 has a smaller diameter, so that gaseous fluid can enter and exit the chamber 84 from the collection chamber 72 around the closure element 78. In this state, the chamber 84 can be pressurized with negative pressure by actuating the vacuum pump 76 and the first switching valve 78. Subsequently, protective gas can be introduced into the chamber 84 by actuating the second switching valve 30. The above-mentioned operations can be repeated until the chamber 84 is as oxygen-depleted as possible, and the closure element 78 can be introduced into the container 68 by actuation of the stopper plunger 44, such that the container 68 is closed. The closure element 78 remains on the container 68.

Subsequently, the stopper plunger can be joined to another closure element 78 and another partially filled container 68 can be provided and the above-described operations repeated until the filling and closure of a batch of filling material is completed.

The areas of the tool unit 18 which, with respect to the fluid supply device 32, are downstream of the filters 64 and 66, that is to say facing the container 68, are referred to collectively as the fluid unit 90. In particular, this fluid unit 90 comprises the collection chamber 72 and fluid line areas, in particular in the form of the branch lines 70, 74.

As can be seen in particular from FIG. 3, the tool unit 18 can be handled as a whole as a module. This module comprises the aforementioned fluid unit 90, the filters 64 and 66, as well as the closing tool 42 and part of the coupling device 16. This unit, shown in FIG. 4, can be handled as a module, that is to say as a whole, and can be connected to the tool receptacle 14 or removed therefrom for sterilization in preparation for a subsequent batch. For these joining operations, a further handling device (not shown) can be used, for example in the form of a second robot arm.

What is claimed is:

1. A closing apparatus (10) for closing pharmaceutical containers (68), the closing apparatus (10) comprising:
   (i) a tool unit (18) including:
      a fluid unit (90), and
      a closing tool (42) for joining a closure element (78) to a pharmaceutical container (68); and
   (ii) a tool receptacle (14),
   wherein the fluid unit (90) has at least two filters (64, 66),
   wherein the tool unit (18) is a module which is repeatedly detachable from and connectable to the tool receptacle (14) by a coupling device (16),
   wherein the fluid unit (90) is configured to apply at least two different gaseous fluids to the pharmaceutical container (68), and
   wherein one of the at least two filters (64, 66) interacts with one of the at least two different gaseous fluids and another of the at least two filters (64, 66) interacts with another of the at least two different gaseous fluids.

2. The closing apparatus (10) according to claim 1, wherein the coupling device (16) has a coupling element (46) and a coupling element receptacle (48), which interact form-fittingly in a state coupled to one another.

3. The closing apparatus (10) according to claim 1, wherein the tool receptacle (14) comprises an actuating device (50) for switching the coupling device (16) between a locking state, in which the module is connected to the tool receptacle (14), and a release state, in which the module is releasable from the tool receptacle (14).

4. The closing apparatus (10) according to claim 1, wherein the module comprises at least one fluid connection (38, 40), the tool receptacle (14) comprises at least one fluid supply device (32), and the at least one fluid connection (38, 40) and the at least one fluid supply device (32) are fluidically connected to each other in a state in which the module and the tool receptacle (14) are connected to each other.

5. The closing apparatus (10) according to claim 1, wherein the tool receptacle comprises an actuator (56) for actuating the closing tool (42).

6. The closing apparatus (10) according to claim 1, wherein the one of the at least two different gaseous fluids is a negative-pressure gas, and the another of the at least two different gaseous fluids is a protective gas.

7. The closing apparatus (10) according to claim 1, wherein the tool receptacle (14) is held on a robot arm (12).

8. The closing apparatus (10) according to claim 1, wherein the closing apparatus (10) has a handling device for handling the module.

* * * * *